United States Patent [19]
Kugai

[11] Patent Number: 5,963,032
[45] Date of Patent: *Oct. 5, 1999

[54] NON-DESTRUCTIVE TESTING EQUIPMENT HAVING SQUID-TYPE SENSOR IN MAGNETIC SHIELD CONTAINER AND OBJECT-MAGNETIZING MAGNETIC FIELD GENERATOR

[75] Inventor: Hirokazu Kugai, Hyogo, Japan

[73] Assignee: Sumitomo Electric Industries, Ltd., Osaka, Japan

[ * ] Notice: This patent is subject to a terminal disclaimer.

[21] Appl. No.: 08/907,616

[22] Filed: Aug. 8, 1997

Related U.S. Application Data

[63] Continuation of application No. 08/273,433, Jul. 11, 1994.

[30] Foreign Application Priority Data

Jul. 12, 1993 [JP] Japan .................................. 5-195124

[51] Int. Cl.$^6$ .......................... G01N 27/90; G01N 27/82; G01R 33/035; G01R 33/12
[52] U.S. Cl. ............................................ 324/240; 324/262
[58] Field of Search ..................................... 324/232, 226, 324/240, 262, 248, 235, 225

[56] References Cited

U.S. PATENT DOCUMENTS

| | | | |
|---|---|---|---|
| 4,734,643 | 3/1988 | Bubenik et al. | 324/232 |
| 5,729,135 | 3/1998 | Kugai | 324/240 |

*Primary Examiner*—Walter E. Snow
*Attorney, Agent, or Firm*—Kerkam, Stowell, Kondracki & Clarke, P.C.; John C. Kerins

[57] ABSTRACT

A nondestructive testing equipment comprises a magnetic sensor located within a magnetic shield container. The magnetic sensor includes a SQUID that is a magnetic sensor having a very high sensitivity. A magnetically uniform inspection zone is formed in the magnetic shield container. While a rod-like material to be tested passes through the inspection zone at a uniform velocity, the magnetic sensor can detect an appreciable magnetic field variation that is caused by impurities or minor defects contained in the object to be tested.

7 Claims, 6 Drawing Sheets

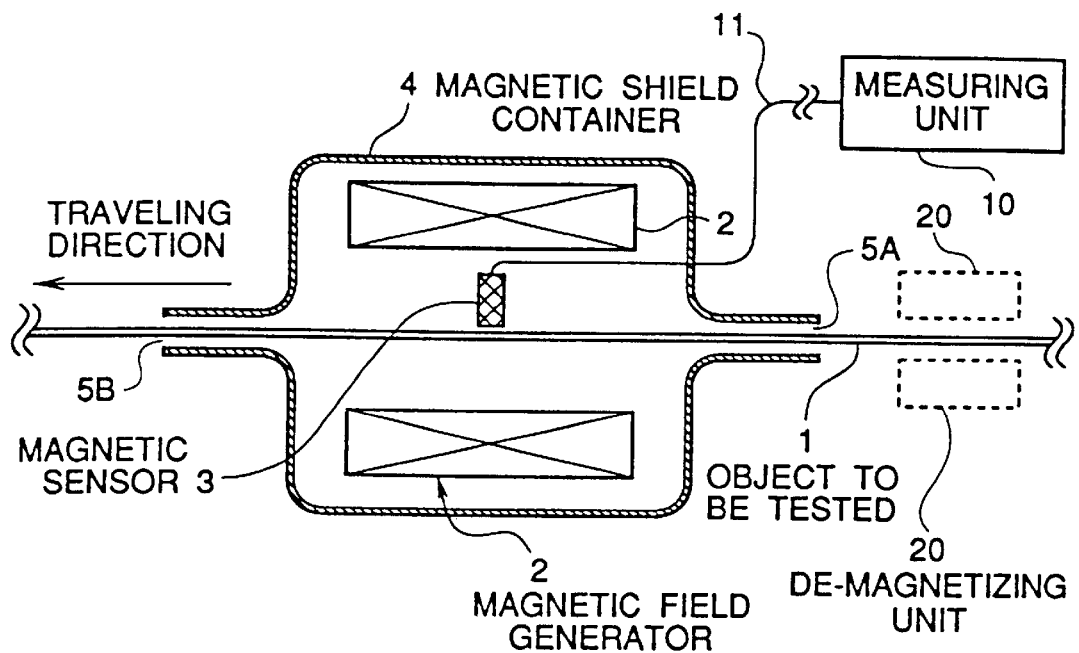
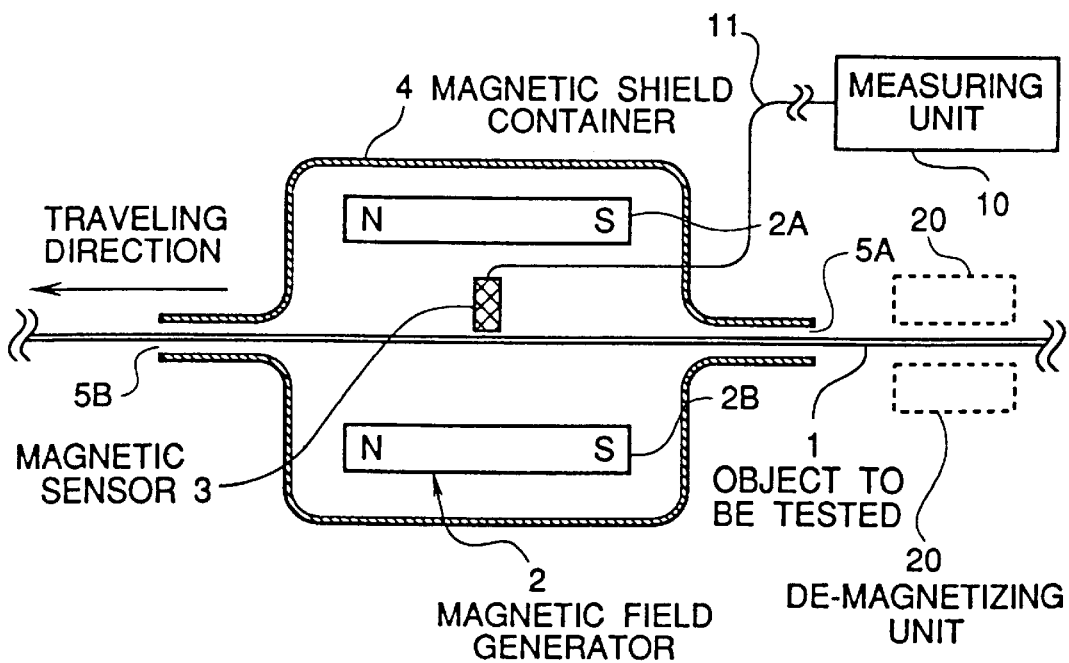

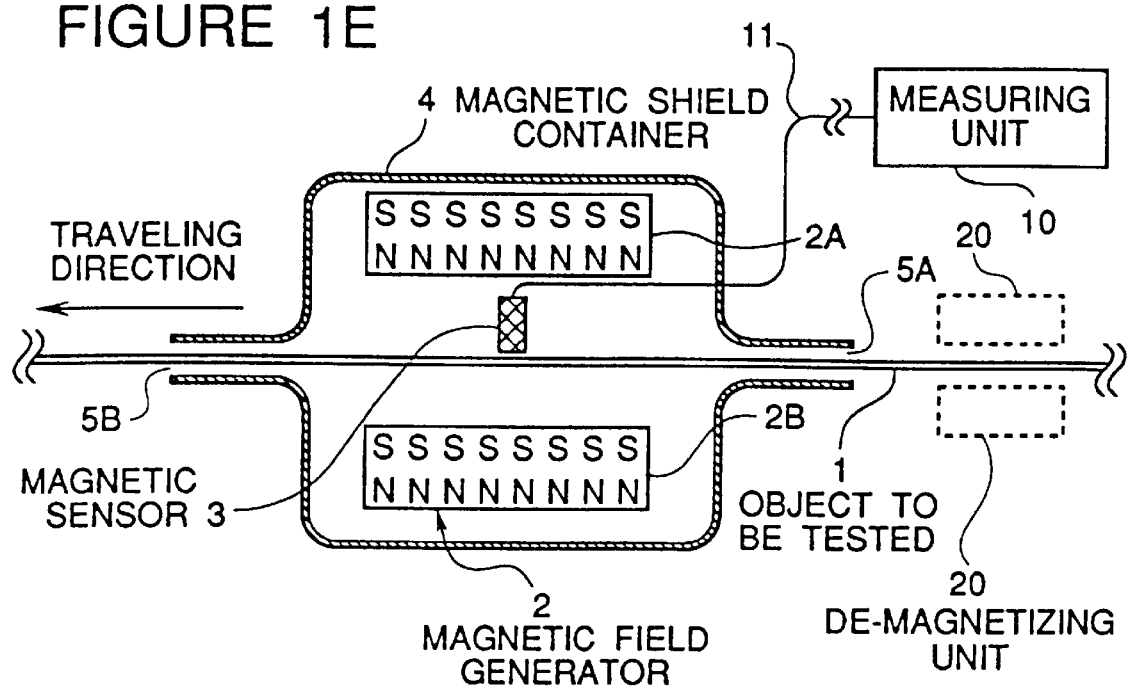
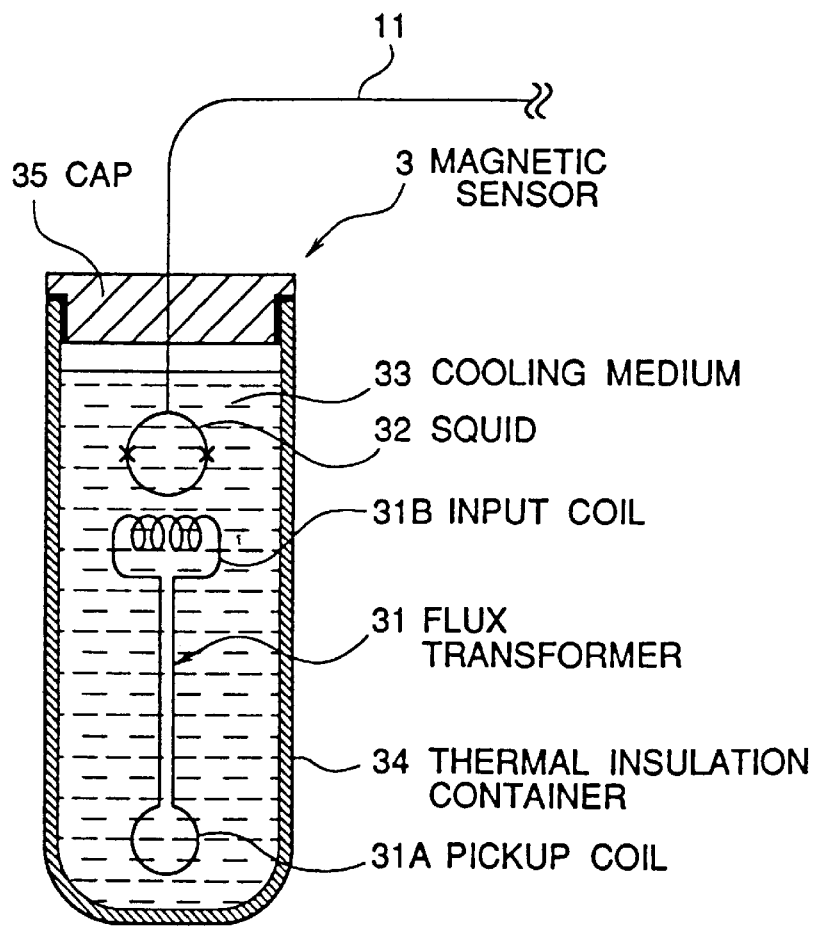

NON-DESTRUCTIVE TESTING EQUIPMENT HAVING SQUID-TYPE SENSOR IN MAGNETIC SHIELD CONTAINER AND OBJECT-MAGNETIZING MAGNETIC FIELD GENERATOR

This application is a continuation of application Ser. No. 08/273,433, filed Jul. 11, 1994.

BACKGROUND OF THE INVENTION

1. Field of the Invention

The present invention relates to a non-destructive testing equipment having a SQUID type magnetic sensor. More specifically, the present invention relates to a new magnetic testing equipment which can continually detect impurities or defects contained in an object to be tested, with high sensitivity.

2. Description of Related Art

Wire-rod materials such as optical fibers, cables and wires, and plate-like metal or ceramics materials which can be used for a body of aircraft or spacecrafts and satellites, have an extremely large length or a large area. On the other hands, extremely small impurities or slight defects included in these materials will results in serious troubles and damages. Therefore, severe quality control has been required for these materials.

In turn, in signal cables composed of signal conductors, insulators and tensile strength members in combination, individual component parts can be tested before the component parts are assembled to a cable. However, there is no method for detecting internal defects or presence of impurities in the cables after the cables have been completed. Therefore, the testing of the completed cables had to rely upon a partially destructive sampling inspection in which one or more cables are sampled from a lot of completed cables, and then, the sampled cables are broken and tested.

Furthermore, wire-like materials and rod-like materials have been continuously produced in an industrial production scale as elongated products, and then, have been used as elongated products. As explained above, if even only a portion of these elongated materials contains a small defect, a total function of these elongated materials is subjected to very serious influence. Accordingly, during a production process, it is desirable to test the whole of the elongated materials. However, there has not yet been a non-destructive testing means that can precisely and efficiently inspect the whole of the elongated materials so as to find out an internal defect during a manufacturing process of the elongated materials.

SUMMARY OF THE INVENTION

It is an object of the present invention to provide a non-destructive testing equipment which has overcome the above mentioned defect of the conventional ones.

Another object of the present invention is to provide a non-destructive testing equipment which can precisely and efficiently inspect an elongated or large product to be tested, so as to continuously find out extremely small impurities or internal defects in the product to be tested, in a manufacturing process of the product to be tested.

The above and other objects of the present invention are achieved in accordance with the present invention by a testing equipment comprising a magnetic shield container defining an inspection zone within an internal space of the magnetic shield container, so that an object to be tested can be positioned in the inspection zone, the magnetic shield container preventing an environment magnetic field from invading the internal space of the magnetic shield container, and a magnetic sensor located in the magnetic shield container and having at least one SQUID (Superconducting Quantum Interference Device), for detecting the magnetic field in the inspection zone, so that the magnetic sensor detects a variation of the magnetic field which is caused by impurities or defects contained in the object to be tested in the inspection zone.

With this arrangement, a minute variation of the magnetic field which is caused by impurities or defects contained in the object to be tested, can be detected by a super high sensitive SQUID type magnetic sensor. Therefore, the impurities of the defects can be precisely and quickly inspected in a non-destructive manner.

In brief, the testing equipment functions as follows. Since the inspection zone is isolated from influence of the environment magnetic field by the magnetic shield container, the inspection zone is magnetically uniform. In other words, a uniform magnetic field is formed in the inspection zone. Here, this "uniform magnetic field" should be understood to include a condition in which no magnetic field exists.

If an object to be tested is located in the inspection zone, some change occurs in the magnetic field in accordance with for example a magnetized condition or a magnetic susceptibility of the object to be tested. However, if the object to be tested contains impurities or defects, the magnetic field shows a unique change which is caused by existence of the impurities or the defects. This unique change of the magnetic field can be sensed by the super high sensitive SQUID magnetic sensor, as a change distinguishable from the change of the magnetic field caused by the object to be tested containing neither impurities nor defects. Therefore, it is possible to detect impurities or defects contained in a magnetized magnetic material.

The change of the magnetic field caused when the object to be tested is located in the inspection zone, is determined by the magnetic susceptibility or the magnetization of the object to be tested. Therefore, if a uniform elongated object to be tested is caused to continuously pass through the inspection zone and if the elongated object to be tested has neither defects nor impurities, the magnetic field is modified by the uniform elongated object but the modified magnetic field is stationary, namely does not change during a continuous passage of the elongated object through the magnetic field. In this case, if a portion including either defects or impurities passes through the inspection zone, the modified magnetic field is disturbed. This disturbance of the magnetic field is detected by the super high sensitive SQUID magnetic sensor, even if it is very slight.

If an elongated object to be tested having a periodically changing shape or property is caused to continuously pass through the inspection zone and if the elongated object to be tested has neither defects nor impurities, the magnetic field is modified by the elongated object, and the modified magnetic field varies periodically. In this case, if a portion including either defects or impurities passes through the inspection zone, the periodically varying magnetic field is disturbed. This disturbance of the magnetic field is detected by the super high sensitive SQUID magnetic sensor, even if it is very slight.

By the way, in the above mentioned testing equipment, the inspection zone, in which the testing is located, is surrounded by the magnetic shield container. Accordingly, the testing can be carried out without influence of an environment magnetic field. For this purpose, the magnetic shield container can be formed of permalloy. Furthermore, the magnetic shield container in the shape of a tube is used preferably so that a very long object to be tested such as a wire, a rod, an elongated plate, can be inspected continually when the very long object to be tested passes through the tube-like magnetic shield container.

One embodiment of the testing equipment in accordance with the present invention further includes a magnetic field generator located within the magnetic shield container, for generating a stable magnetic field in the inspection zone. In this case, a magnetic field is positively created in the inspection zone that is isolated from influence of the environment magnetic field by the magnetic shield container. If an object to be tested is located in the inspection zone, some change occurs in the magnetic field in accordance with for example a magnetized condition or a magnetic susceptibility or a magnetization of the object to be tested.

However, the object to be tested contains impurities or defects, the magnetic field shows a unique change which is caused by existence of the impurities or the defects. This unique change of the magnetic field can be sensed by the super high sensitive SQUID magnetic sensor, as a change distinguishable from the change of the magnetic field caused by the object to be tested containing neither impurities nor defects.

In another embodiment of the testing equipment in accordance with the present invention, there is additionally provided a mean located at an outside of the magnetic shield container, for de-magnetizing the object to be tested before the object to be tested is introduced into the magnetic shield container. In this case, even if the object to be tested has been magnetized at random or non-uniformly, the at-random or non-uniform magnetization is cancelled before the object to be tested is introduced into the magnetic shield container, so that the magnetic sensor can detect only the magnetic variation caused by existence of the impurities or the defects.

Alternatively, the testing equipment further includes a magnetic field generator located at an outside of the magnetic shield container, for magnetizing the object to be tested before the object to be tested is introduced into the magnetic shield container. In this case, if an object to be tested is located in the inspection zone, some change occurs in the magnetic field in accordance with the magnetized condition of the object to be tested. However, if the object to be tested contains impurities or defects, since the magnetized condition of the object to be tested is different, the magnetic field in the inspection zone shows a unique change which is caused by existence of the impurities or the defects. This unique change of the magnetic field can be sensed by the super high sensitive SQUID magnetic sensor, as a change distinguishable from the change of the magnetic field caused by the object to be tested containing neither impurities nor defects.

In one preferred embodiment of the non-destructive testing equipment in accordance with the present invention, the SQUID formed of an oxide superconducting thin film is preferably used. In general, oxide superconducting materials become a superconducting state at a temperature obtained by an inexpensive liquid nitrogen. Accordingly, a running cost of the equipment becomes lower and a handling in operation becomes easy too.

In another preferred embodiment of the non-destructive testing equipment in accordance with the present invention, a plurality of magnetic sensors can be arranged, for example in a direction perpendicular to the direction of movement of the object to be tested. This arrangement makes it possible to inspect a wide object to be tested.

When the object to be tested has an elongated shape as a pipe or a rod, it is desirable that a plurality of magnetic sensors are located to surround the object to be tested in a plane perpendicular to the direction of movement of the object to be tested. In this case, a through-hole through which the object to be tested can pass, is formed in a thermal insulation container accommodating a cooling medium and the magnetic sensors.

As mentioned above, the testing equipment in accordance with the present invention can non-destructively inspect an extremely minute defects or impurities contained in an object to be tested. Furthermore, this non-destructive testing equipment can detect not only existence of defects or impurities, but also a position of a defect or an impurity and distribution of defects or impurities. Accordingly, it is possible to inspect all of large or long products during a manufacturing process.

The above and other objects, features and advantages of the present invention will be apparent from the following description of preferred embodiments of this invention with reference to the accompanying drawings.

BRIEF DESCRIPTION OF THE DRAWINGS

FIGS. 1B, 1C, 1D and 1E are diagrammatic sectional views showing second to fifth embodiments of the non-destructive testing equipment in accordance with the present invention;

FIG. 2 is a sectional view of an example of the magnetic sensor which can be used preferably in the testing equipment shown in FIGS. 1;

DESCRIPTION OF PREFERRED EMBODIMENTS

Figure 1A:
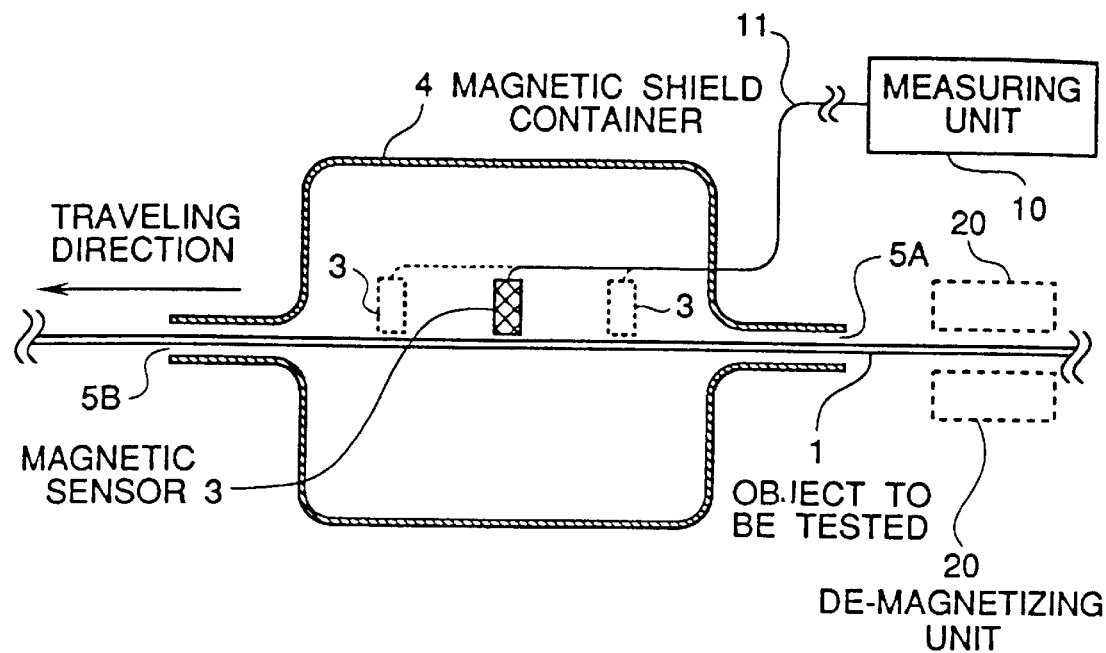
FIG. 1A is a diagrammatic sectional view showing a first embodiment of the non-destructive testing equipment in accordance with the present invention.

Referring to FIG. 1A, there is shown a diagrammatic sectional view showing a first embodiment of the non-destructive testing equipment in accordance with the present invention.

The shown non-destructive testing equipment comprises a magnetic sensor 3 located in a magnetic shield container 4. The magnetic shield container 4 is in the shape of a pipe having a pair of narrowed-down open ends 5A and 5B. An object 1 to be tested, for example in the form of a continuous rod or wire, travels continually from one open end 5A to the other open end 5B of the magnetic shield container 4 by a feeding means (not shown).

The magnetic sensor 3 is arranged near to the traveling path of the object 1 to be tested, and connected through a cable 11 to a suitable measuring unit 10 located at an outside of the magnetic shield container 4. In place of only one magnetic sensor 3, a plurality of magnetic sensors 3 can be located along the traveling path of the object 1 to be tested, as shown in a ghost line in FIG. 1A.

The magnetic sensor 3 used in the testing equipment comprises at least one SQUID. The SQUID can function alone as a magnetic sensor, but generally, it is used with a flux transformer coupled magnetically with the SQUID. Because, sensitivity of the SQUID as a magnetic sensor can be improved by combination with the flux transformer.

Referring to FIG. 2, there is shown the magnetic sensor which can be used in the testing equipment shown in FIG. 1. This magnetic sensor comprises a flux transformer 31 and a SQUID 32, both located in a non-magnetic thermal insulation container 34 having a closed bottom end and an open end hermetically closed with a cap 34A. For example, the flux transformer 31 has a single-turn pickup coil 31A and a multi-turn input coil 31B interconnected to form a closed loop. The flux transformer 31 is magnetically coupled to the SQUID 32. The SQUID 32 is connected to the measuring unit 10 (not shown in FIG. 2) through the cable 11.

An internal space of the thermal insulation container 34 is filled with a cooling medium 33, which can be exemplified by liquid nitrogen, liquid hydrogen, liquid helium or the likes. Material of this cooling medium 33 has to be selected according to a superconducting material used for constituting the SQUID 32.

By the way, a pick up coil of the flux transformer 31 may be formed by a pair of coils having their winding directions opposite to each other, so that the whole of the magnetic sensor is in the form of a so-called "gradiometer".

The first embodiment shown in FIG. 1A is effective in detecting defects or impurities included in an objected to be tested, in the case that the objected to be tested is uniformly magnetized or in the case that the impurities included in the objected to be tested are magnetized.

Figure 1B:
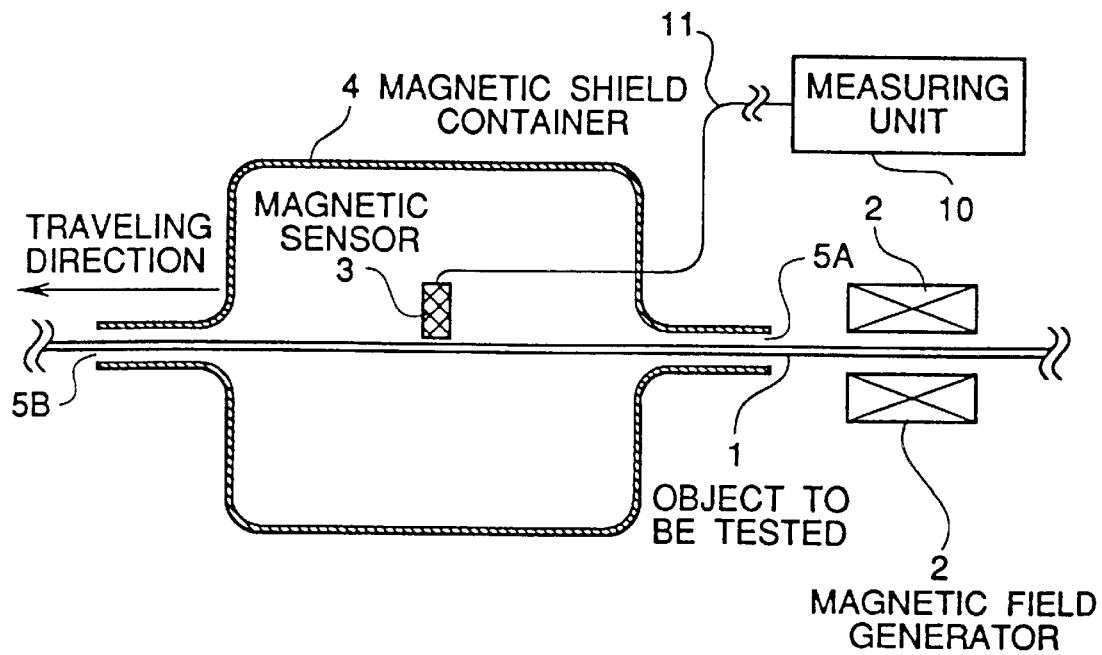

As shown in FIG. 1B, which is a diagrammatic sectional view showing a second embodiment of the non-destructive testing equipment in accordance with the present invention, a magnetic field generator 2 can be located before the one open end 5A of the magnetic shield container 4, so that the object to be tested is uniformly magnetized before the object to be tested is introduced into the magnetic shield container.

In the embodiment shown in FIG. 1B, the magnetic field generator 2 is formed of a solenoid surrounding the traveling path of the object 1 to be tested so that a magnetic field is created in parallel to the traveling path of the object 1 to be tested.

The embodiment shown in FIG. 1B is effective in forcibly magnetizing the objected to be tested in the case that a magnetic objected to be tested is not magnetized or in forcibly magnetizing the impurities included in the objected to be tested in the case that the impurities included in the objected to be tested are a magnetic material but have not been magnetized.

Alternatively, as shown in FIG. 1C, which is a diagrammatic sectional view showing a third embodiment of the non-destructive testing equipment in accordance with the present invention, the magnetic field generator 2 can be located within the magnetic shield container 4, so that a uniform magnetic field is positively created within the magnetic shield container. In the embodiment shown in FIG. 1C, the magnetic field generator 2 is formed of the solenoid surrounding the traveling path of the object 1 to be tested so as to create a magnetic field in parallel to the traveling path of the object 1 to be tested.

However, the magnetic field generator 2 can be formed of a pair of permanent magnets, as shown in FIG. 1D, which is a diagrammatic sectional view showing a fourth embodiment of the nondestructive testing equipment in accordance with the present invention. In the fourth embodiment shown in FIG. 1D, a pair of permanent magnets 2A and 2B are located in such a manner that the object to be tested is interposed between the pair of permanent magnets 2A and 2B. In addition, the pair of permanent magnets 2A and 2B are so directed in polarity that a magnetic field is created in parallel to the traveling path of the object 1 to be tested.

Furthermore, as shown in FIG. 1E, which is a diagrammatic sectional view showing a fifth embodiment of the non-destructive testing equipment in accordance with the present invention, the pair of permanent magnets 2A and 2B can be so directed in polarity that a magnetic field from one to the other of the permanent magnets 2A and 2B passes through the object 1 to be tested, perpendicularly to the traveling path of the object 1 to be tested.

The above mentioned third to fifth embodiments having the magnetic field generator is located within the magnetic shield container 4, makes it possible to detect defects or impurities included in a non-magnetic objected to be tested, On the other hand, in the first and second embodiments, since no magnetic field generator is located within the magnetic shield container 4, the magnetic sensor 3 is subjected to no noise from a magnetic field generator.

By the way, when the object to be tested is made of magnetic material the object to be tested may have in some cases been magnetized non-uniformly. In this case, even if there was neither defect nor impurity in the object to be tested, the internal magnetic field of the magnetic shield container would be disturbed. Accordingly, when the object to be tested is formed of a magnetic material, it is desirable that a de-magnetizing unit 20 is provided in an intake section, as shown in ghost line in FIGS. 1A, 1C, 1D and 1E. As known to persons skilled in the art, the demagnetizing unit 20 is configured to apply an alternating magnetic field having the magnitude which is large at its inlet side (remote from the magnetic shield container 4) and gradually becomes small and finally zero at its outlet side (near to tie magnetic shield container 4).

Principle of operation of tile testing equipment shown in FIG. 1 will be now described with reference to FIGS. 3A through 3C.

Figure 3A:
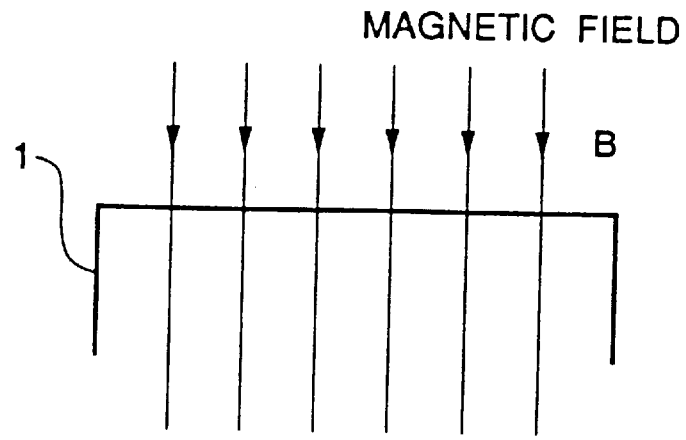
FIGS. 3A, 3B and 3C are magnetic field diagrams illustrating a defect inspection theory of the non-destructive testing equipment in accordance with the present invention.

As shown in the FIG. 3A, assume that a uniform magnetic field B exists. When the object 1 to be tested is located within the uniform magnetic field B, the magnetic field changes in accordance with a magnetization or a magnetic susceptibility of the object 1 to be tested, but becomes stable if the object 1 to be tested is stationary. If the object 1 to be tested is caused to move through the uniform magnetic field at a constant velocity, the magnetic field is stable or stationary (in the case that a uniform elongated object having neither defects nor impurities is caused to continuously pass through the magnetic field), or the magnetic field constantly changes at a constant period (in the case that the elongated object has a periodically changing repeated shape).

Figure 3B:
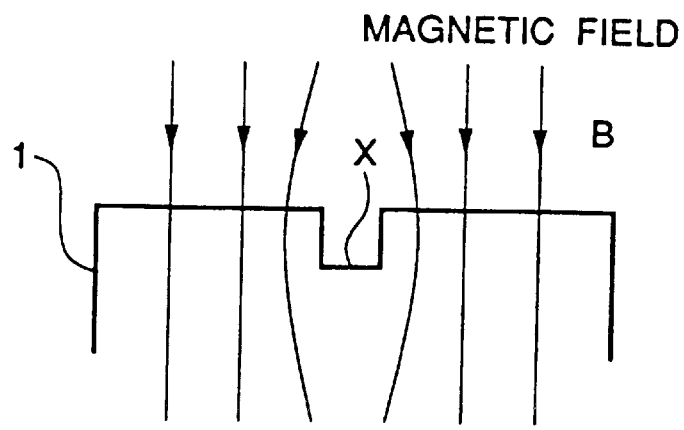
Figure 3C:
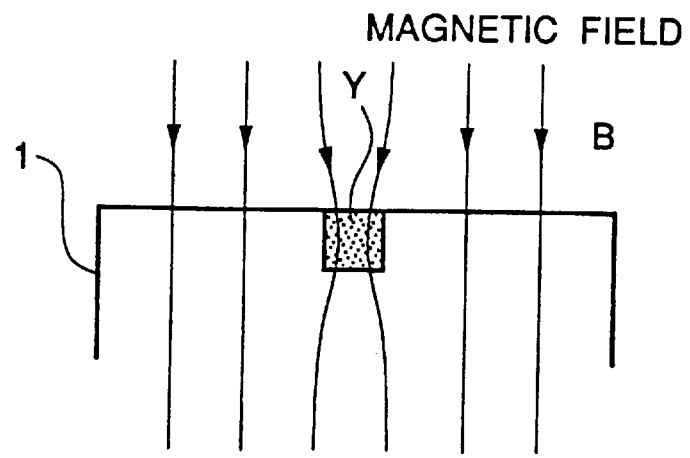

When the object 1 to be tested contains a defect X as shown in the FIG. 3B or an impurity Y as shown in the FIG. 3C, the magnetic field B shows an appreciable change in accordance with the defect X or a magnetic susceptibility or a magnetization of the impurity Y. The appreciable change of the magnetic field B is detected by the magnetic sensor, which outputs the result of the detection in the form of a voltage signal.

Figure 4A:
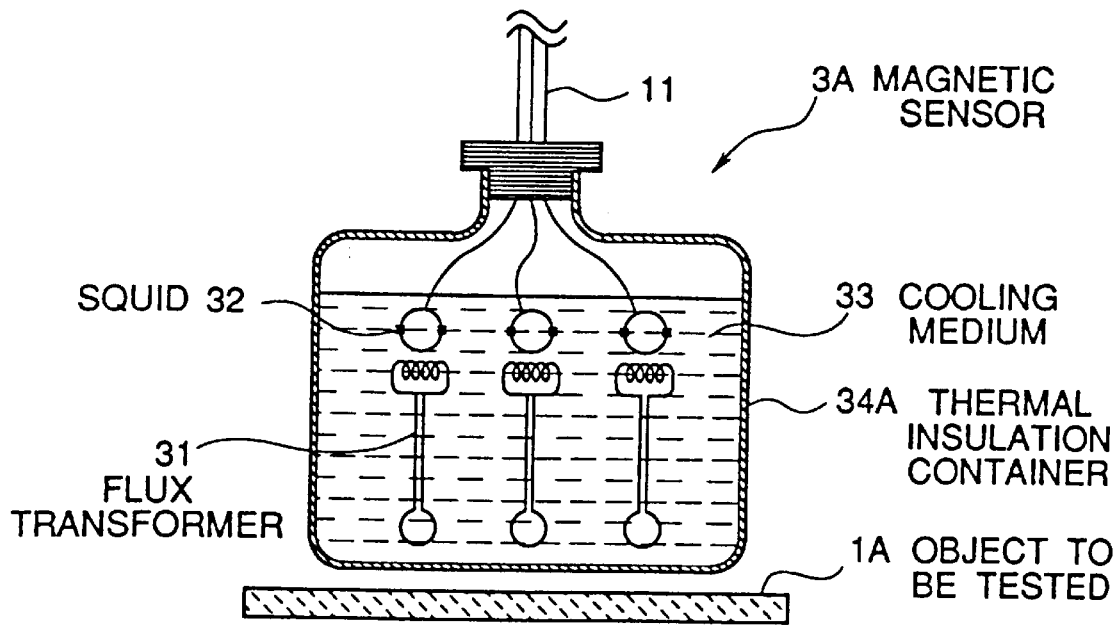
FIGS. 4A and 4B are sectional views of specific examples of the magnetic sensor used in the non-destructive testing equipment in accordance with the present invention.
Figure 4B:
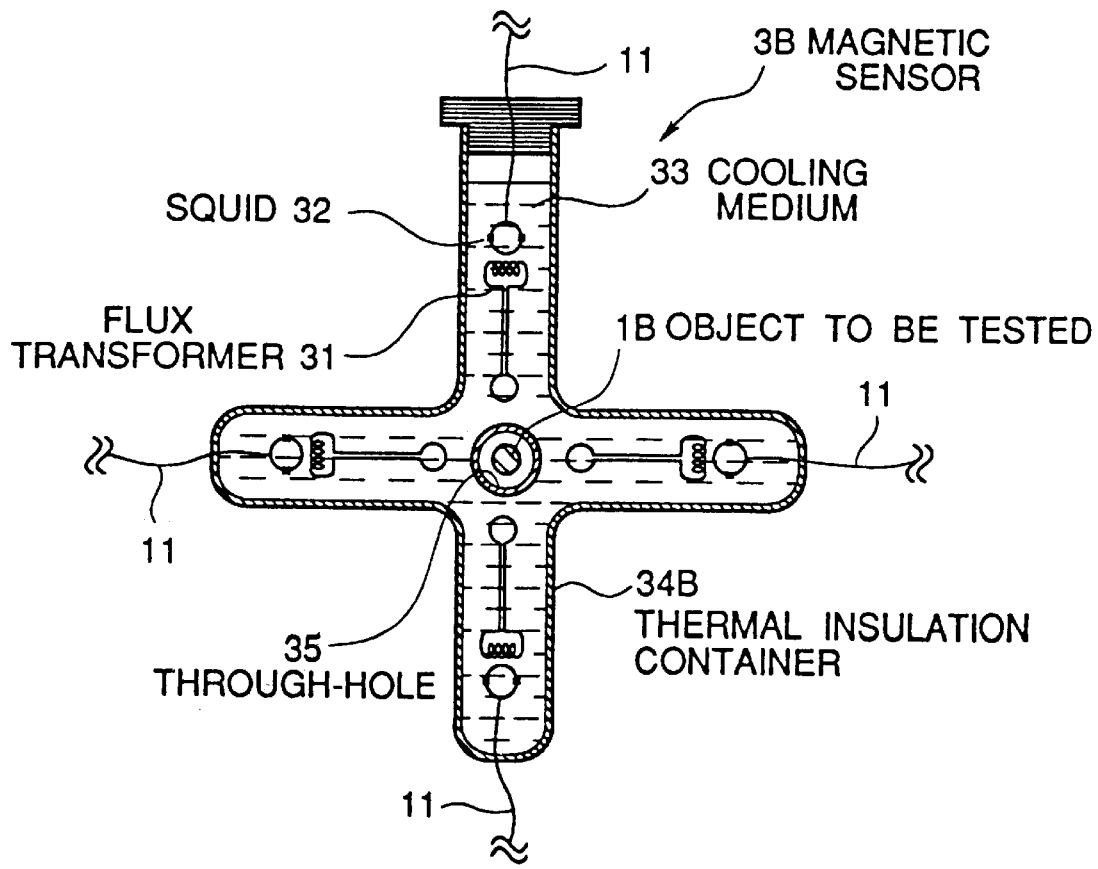

Referring to FIGS. 4A and 4B, there are shown other constructions of the magnetic sensor that can be used in the testing equipment in accordance with the present invention. FIGS. 4A and 4B are sectional views taken along in a plane perpendicular to the traveling direction of the object 1 to be tested.

A magnetic sensor 3A shown in FIG. 4A is configured to inspect an object 1A to be tested in the form of a wide plate-like material. For this purpose, this magnetic sensor 3A comprises a plurality of unitary magnetic sensors (each composed of one SQUID and one flux transformer magnetically coupled thereto) arranged on a straight line in parallel to a plane of the plate-like object 1A to be tested and perpendicular to the traveling direction of of the object 1A to be tested. The flux transformers 31 and the SQUIDs 32 are housed in a thermal insulation container 34A, and an internal space of the thermal insulation container 34A is filled with a cooling medium 33.

The magnetic sensor of this construction can detect a location of defects and/or impurities over a full width of the plate-like object 1A to be detected.

A sensor 3B shown in FIG. 4B is configured to inspect an object 1B to be tested in the form of a tube or a rod. This sensor comprises a thermal insulation container 34B accommodating a cooling medium 33 and a plurality of SQUIDs 32 coupled to a corresponding number of flux transformers 31, similarly to the sensor shown in FIG. 4A.

The thermal insulator container 34 comprises a through-hole 35 as a passage allowing the object 1 to be tested to pass therethrough. The plurality of SQUIDs 32 and flux transformers 31 are arranged in a plane perpendicular to the travelling direction of the object 1 to be tested, so as to completely surround the through-hole 35 at equal or at-random angular intervals. Accordingly, defects or impurities in the rod-like or pipe-like object 1B to be tested can be detected from its whole periphery along its length.

Figure 5:
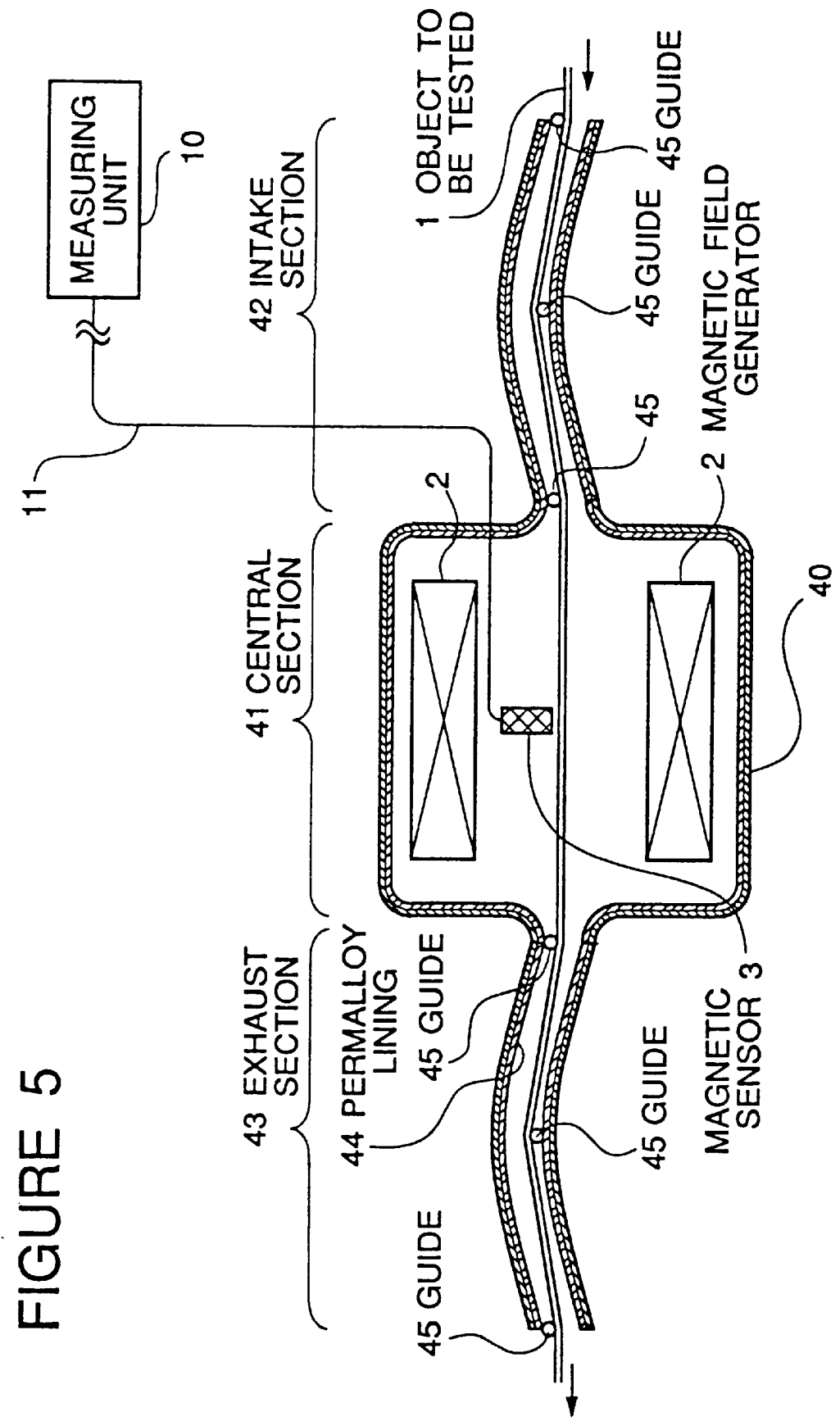
FIG. 5 is a diagrammatic sectional view of still another embodiment of the non-destructive testing equipment in accordance with the present invention, comprising a magnetic shield container of another shape.

FIG. 5 shows one specific construction of the testing equipment comprising a magnetic shield container of another shape. The testing equipment shown in FIG. 5 has the same construction as that of the testing equipment shown in the FIG. 1, excepting for the shape of the magnetic shield container. Therefore, elements similar or corresponding to those shown in FIG. 1 are given the same Reference Numerals, and explanation thereof will be omitted. Namely, only the magnetic shield container of the shown testing equipment will be described.

In this testing equipment, a magnetic shield container 40 is constituted by a central section 41 actually defining an inspection zone therein, an intake section 42 coupled to one end of the central section 41, for guiding and introducing an object 1 to be tested, into the central section 41, and an exhaust section 43 coupled to the other end of the central section 41, for outputting or extracting the object 1 to be tested, from the central section 41.

The central section 41 has a large section for accommodating the magnetic field generator 2 and the magnetic sensor 3. When a continuing long object 1 is tested by the testing equipment having this magnetic shield container 40, the object to be tested is introduced from the intake section 42 into the central section 41 and fed out of the central section 41 through the exhaust section 43.

The magnetic shield container 40 has its whole inner surface line with a permalloy layer 44. Therefore, an environment magnetic field is prevented from invading into the central section 41. Of course, other magnetic materials can be used instead of the permalloy.

At the same time, the intake section 42 and the exhaust section 43 of this magnetic shield container 4 are long along the traveling path of the object to be tested, and also, are so bent or curved along the traveling path that an internal space of the central section 41, particularly the magnetic sensor 3, cannot be looked from an outer end of each of the intake section 42 and the exhaust section 43. With this arrangement, the elongated object to be tested can be continuously fed into the internal space of the magnetic shield container 40 and fed out of the internal space of the magnetic shield container 40, and at the same time, the environment magnetic field in no way invades the inside of the central section 41. Accordingly, the internal space of the central section 41 can be magnetically substantially perfectly shielded. Since the traveling path of the object to be test is bent in the intake section 42 and the exhaust section 43, it is preferable that guide means 45 are provided in the intake section 42 and the exhaust section 43 so that the object 1 to be tested is smoothly guided by the guide means 45.

Accordingly, if this non-destructive testing equipment is installed in a rod-like material manufacturing line, the non-destructive testing equipment can be continuously operated without stopping the rod-like material manufacturing line.

The present invention has thus been shown and described with reference to the specific embodiments. However, it should be noted that the present invention is in no way limited the details of the illustrated structures but converts and modifications may be made within the scope of the appended claims.

I claim:

1. A non-destructive testing equipment comprising:
   a magnetic shield container defining an inspection zone within an internal space of said magnetic shield container, so that an object to be tested can be positioned in said inspection zone, said magnetic shield container preventing an environment magnetic field from invading said internal space of said magnetic shield container;
   magnetic sensor means for detecting a magnetic field in said inspection zone, and for detecting variations in said magnetic field caused by impurities or defects in said object, said magnetic sensor means being located in said magnetic shield container and having at least one SQUID; and
   a magnetic field generator located at an outside of said magnetic shield container, for producing a magnetized state in said object to be tested before said object to be tested is introduced into said magnetic shield container whereby said magnetic sensor means, when said magnetized state has been produced in said object to be tested and when said object is then introduced into said magnetic shield container, detects variations in said magnetic field caused by variations in said magnetized state of said object, said variations in said magnetized state being generated by impurities or defects in said object.

2. A testing equipment according to claim 1 wherein said object to be tested is moved to pass through said inspection zone, so that said magnetic sensor detects a variation of the magnetic field which is caused by impurities or defects contained in said object to be tested passing through said inspection zone.

3. A testing equipment according to claim 1 wherein said magnetic shield container is in the form of a pipe having a pair of open ends, so that said object to be tested can be introduced from one of said pair of open ends into said magnetic shield container so as to go out from the other open end, whereby an elongated objected can be continuously detected by said magnetic sensor with in said magnetic shield container.

4. A testing equipment according to claim 1 wherein a plurality of magnetic sensors are arranged in a traveling direction of said object to be tested.

5. A testing equipment according to claim 1 a plurality of magnetic sensors arranged in a direction perpendicular to a traveling direction of said object to be tested.

6. A testing equipment according to claim 1 wherein said magnetic sensor accommodated in a thermal insulation container filled with a cooling medium, and said thermal insulation container has a through-hole allowing said object to be tested to pass through said through-hole, and wherein a plurality of magnetic sensors are arranged in said thermal insulation container to surround said through-hole.

7. A testing equipment according to claim 1 wherein said magnetic shield container comprises a central section accommodating said magnetic sensor, an intake section coupled to one end of said central section, for allowing said object to be tested to be fed through said intake section into the central section, and an exhaust section coupled to the other end of said central section, for allowing said object to be tested to be exhausted from said central section through said exhaust section, a passage of said intake section and said exhaust section being so bent that an inside of said central section cannot be looked from an outer end of each of said intake section and said exhaust section.

* * * * *